United States Patent
Hagopian

(12) 
(10) Patent No.: US 6,581,775 B1
(45) Date of Patent: Jun. 24, 2003

(54) METHOD OF EXTERNAL GENITAL CLEANSING AND PROPHYLACTIC KIT

(76) Inventor: Garo Hagopian, 1034 W. Sheila Ct., Montebello, CA (US) 90640

( * ) Notice: Subject to any disclaimer, the term of this patent is extended or adjusted under 35 U.S.C. 154(b) by 0 days.

(21) Appl. No.: 09/927,944

(22) Filed: Aug. 10, 2001

(51) Int. Cl.⁷ .......................... A61K 9/08; B65D 85/00
(52) U.S. Cl. ................ 206/572; 206/69; 206/570; 206/581; 604/290
(58) Field of Search .............. 206/69, 438, 570–572, 206/581, 812; 128/844; 604/290

(56) References Cited

U.S. PATENT DOCUMENTS

| | | | |
|---|---|---|---|
| 2,339,283 A | * 1/1944 | Mendel | 206/69 |
| 2,391,094 A | * 12/1945 | Karg | 206/570 |
| 4,848,588 A | * 7/1989 | Rasmussen | 206/570 |
| 4,892,188 A | * 1/1990 | Meadows | 206/69 |
| 4,925,033 A | 5/1990 | Stoner | |
| 4,974,730 A | * 12/1990 | Deruysscher | 206/812 |
| 5,244,096 A | 9/1993 | Stoner | |
| 5,314,917 A | * 5/1994 | Michaels et al. | 514/556 |
| 5,326,788 A | * 7/1994 | Meruelo et al. | 514/732 |
| 5,624,675 A | * 4/1997 | Kelly | 424/405 |
| 5,753,246 A | * 5/1998 | Peters | 424/404 |
| 6,139,848 A | * 10/2000 | Ahmad et al. | 424/400 |
| 6,239,182 B1 | * 5/2001 | Zaneveld et al. | 514/764 |
| 6,297,278 B1 | * 10/2001 | Michaels et al. | 514/556 |
| 6,302,108 B1 | * 10/2001 | Levine | 128/830 |
| 6,342,537 B1 | * 1/2002 | Thomsen et al. | 514/724 |
| 2002/0151521 A1 | * 10/2002 | Burke et al. | 514/54 |

OTHER PUBLICATIONS

S. Baron, J. Poasr, D. Nguyen, and M. W. Cloyd, "Practical Prevention of Vaginal and Rectal Transmission of HIV by Adapting the Oral Defense: Use of Commercial Lubricants," *AIDS Research and Human Retroviruses*, vol. 17, No. 11, 2001, pp. 997–1002, USA.

\* cited by examiner

*Primary Examiner*—Jim Foster
(74) *Attorney, Agent, or Firm*—Michael Blaine Brooks, P.C.; Michael B. Brooks

(57) ABSTRACT

A method of external genital cleansing and prophylactic kit are disclosed. The kit includes wipes having topical microbicides, personal lubricants, sterile water or sterile water-based solutions disposed on or impregnated therein. The wipes are packaged in conjunction with a condom and when used in accordance with the teaching of this invention work to inhibit transmission of STDs particularly including HIV. Wipes provided in the kit may be used to cleanse the external portions of the genitals before application of the provided condom. After removal of the condom, one or more wipes are to be used to cleanse the external portions of the genitals.

6 Claims, 1 Drawing Sheet

METHOD OF EXTERNAL GENITAL CLEANSING AND PROPHYLACTIC KIT

BACKGROUND

The present invention relates generally to a method of external genital cleansing using a prophylactic kit and more specifically to a combination of one or more condoms and one or more wipes as the kit and the method of use of combinations of these articles for purposes of external genital cleansing intended to enhance hygiene and thereby reduce the possibility of infection by sexually transmitted diseases (STDs) particularly including the Human Immunodeficiency Virus (HIV).

It is generally understood that safe sex is the practice of intimate human sexual intercourse with safeguards placed with the intent of minimizing the transmission of a number of diseases that can occur from such intimate contact with an infected partner. Accordingly, substantive hygienic precautions are necessary components of preserving the health of either partner in the practice of safe sex. In addition to the cleansing of genitals and the absence of open wounds about the genital area, a condom is commonly used as an effective physical barrier for the prevention of both (a) conception and (b) the transmission of microbes through skin or mucosal contact between partners or through the exchange of seminal and vaginal fluids. Also commonly used in the practice of safe sex are vaginal applications of various preparations with either spermicidal or lubricating properties, or both.

Acquired Immune Deficiency Syndrome (AIDS) is a severe immunological disorder that is the final and most serious stage of the HIV disease. The retrovirus, HIV, causes a defect in the cell-mediated immune response that is manifested by increased susceptibility to opportunistic infections and to certain rare cancers, especially Kaposi's sarcoma. HIV can be transmitted via blood transfusions, the sharing of injection needles, through a pregnant or nursing mother to her child, and, in rare instances, through donated semen and organs and through accidental needle sticks. That being said, HIV is transmitted primarily via venereal routes. That is, the chief way of transmitting HIV is through unsafe sexual contact with an infected partner. HIV can be found in the saliva, tears, nervous system tissue, blood, semen (including pre-seminal fluid), vaginal fluid, and breast milk of an infected person. However, only blood, semen, vaginal secretions, and breast milk have been proven to transmit the infection to others.

Recent medical research casts doubt on the effectiveness of the topical microbicide nonoxynol-9 when used in the vagina or rectum to prevent HIV transmission in humans. The irritating side effect nonoxynol-9 has on the mucosal tissues of the vagina and rectum appears to create opportunities for HIV infection. The research teaches away from the use of irritating topical microbicides such as povidone-iodine solutions and nonoxynol-9 where in practical use, they are expected to enter the vagina or rectum preceding or during sexual activity. Moreover, the results of the research indicate that the use of nonirritating, over-the-counter lubricants should be considered for human field trials in the inhibition of HIV production. (See, for example, S. Baron, J. Poast, D. Nguyen, and M. W. Cloyd, "Practical Prevention of Vaginal and Rectal Transmission of HIV by Adapting the Oral Defense: Use of Commercial Lubricants," *AIDS Research and Human Retroviruses*, Volume 17, Number 11, 2001, pp. 997–1002.)

Presently, most retail pharmacies and a great number of grocery and general retail stores offer hygienic wipes along with vaginal lubricants with advertising and trade dress particularly targeting the female consumer. These wipes are individually packaged and sold over the counter in bulk quantities and are designed to be used to clean the substantially external portions of the female genital region. These wipes may also contain microbicides such as nonoxynol-9. These wipes are packaged so as to remain moist within the package and may be scented. One uses the wipes by opening the package, unfolding the wipe, and then applying the wipe as one does a towelette.

It is generally understood that a condom is as a flexible sheath, usually made of thin rubber or latex, designed to cover the penis during sexual intercourse and is worn either for contraceptive purposes or as a barrier device for preventing sexually transmitted diseases, or both. Most condoms are individually packaged and may be obtained with a pre-coating of a spermicidal lubricant. Latex condoms have been shown to be an effective barrier to the transmission of STDs including HIV. That is, if properly applied and properly removed, the use of condoms alone works to prevent sexually transmitted diseases specifically during intercourse. A problem arises in collateral contact of those surfaces or fluids not protected or blocked by the condom barrier. An additional problem arises in that sexual activity before, during, and after intercourse can include a variety of acts beyond coitus. These acts of intimate sexual contact may also give rise to increasing the risk of transmitting STDs including HIV.

U.S. Pat. Nos. 4,925,033 and 5,244,096 to F. L. Stoner disclose a kit for the cleaning of the genital region before and after intercourse principally with povidone-iodine solution, and the cleaning of the mouth with a mouthwash and a toothbrush. While Stoner discloses the application of povidone-iodine solution with a towelette, Stoner does not disclose the inclusion of one or more wipes containing a povidone-iodine solution as part of the kit. In addition, while Stoner discloses the inclusion of a detergent with the povidone-iodine solution, Stoner does not anticipate the irritating effects of the solution on mucosal tissues collaterally contacted in the cleaning process; irritating effects that work against HIV transission.

An object of the present invention is to provide for the convenient cleansing of the external genital region with wipes of selected solutions accompanied by use of one or more included condoms and, through the use of the prophylactic kit contents, thereby reduce the risk of STD, and particularly HIV, transmission. Thus, from the perspective of ease of use, the knowledge of the irritating qualities of povidone-iodine, and the research indicating that human saliva is effective in the natural inhibition of HIV transmission through the targeting of the transmitting infected leukocytes and any cell-fee HIV in seminal fluids, a mouthwash and toothbrush are neither needed nor applied in the present invention.

There remains the need for a condom and one or more hygienic wipes that are conveniently packaged together; the contents of which can be used before and after sexual contact to prevent transmission of STDs, particularly including HIV, while cleaning the genital region with minimal irritation.

The present invention satisfies that need with a method of genital cleansing and prophylactic kit comprised of a one or more first wipes containing an over-the-counter, nonirritating lubricant such as Vagisil® Intimate Moisturizer, Astroglide® Personal Lubricant or ViAmor® Vaginal Moisturizer disposed on or impregnated therein and one or more second wipes preferably containing water-based glycerol and nonoxynol-9 disposed on or impregnated therein for controlled solution application. The user may use a second wipe, or a first wipe, or both in succession, to cleanse the genital region topically in advance of sexual contact and the application of one or more condoms. After the application of one or more condoms, the completion of male climax, and the removal of the one or more condoms, the genital region may then be cleansed with a first wipe or second wipe or both in succession, preferably a second wipe followed by a first wipe. In all cases, while the second wipe may be used optionally, the first wipe is to be used for effective HIV inhibition in the maintenance of genital hygiene with minimal irritation to mucosal tissues affected by collateral contact in the cleaning process. Where wash facilities may not be readily available, a third wipe may be used that is comprised of sterile water or a non-irritating, sterile water-based solution for mild, nonirritating cleansing.

SUMMARY OF THE INVENTION

A method of external genital cleansing and prophylactic kit are disclosed. The kit includes wipes having an over-the-counter lubricant such as Vagisil® Intimate Moisturizer, Astroglide® Personal Lubricant or ViAmor® Vaginal Moisturizer disposed on or impregnated therein. The wipes may be individually packaged and placed with a packaged latex condom as a kit. Where extensive external cleansing may be required, the kit may also include wipes preferably having water-based glycerol and nonoxynol-9 disposed on or impregnated therein. Where wash facilities may not be readily available, a third wipe that is comprised of sterile water or a non-irritating, sterile water-based solution may be included in the kit. The invention further comprises the method by which the contents of the prophylactic kit are used.

DETAILED DESCRIPTION

In a first embodiment, the first wipe solution contains an over-the-counter lubricant such as Vagisil® Intimate Moisturizer or alternatively Astroglide® Personal Lubricant or ViAmor® Vaginal Moisturizer. Through medical research, these products have recently been found to decrease the topical transmission of HIV without the irritating effects of nonoxynol-9, povidone-iodine solutions and like products. Three individually sealed first wipes, containing the over-the-counter lubricant, are combined with three conventionally rolled and sealed condoms in the prophylactic kit of the present invention.

Figure 1:
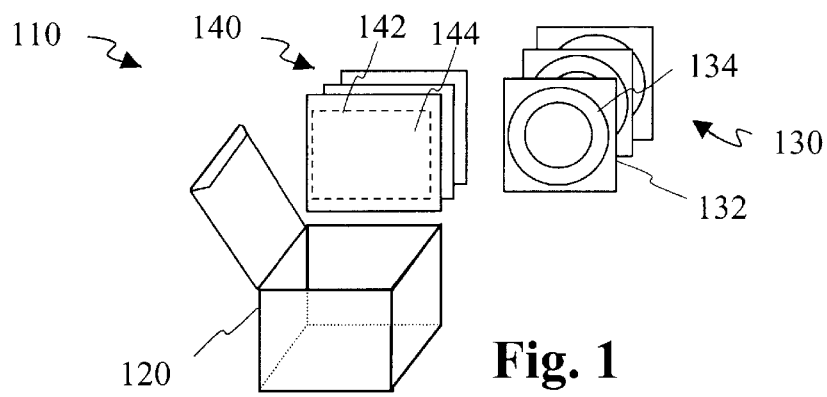
FIG. 1 is an exploded view of the genital cleansing and prophylactic kit illustrating a combination of condoms and wipes of a preferred embodiment.

FIG. 1 is an exploded assembly of a preferred embodiment of the cleansing and prophylactic kit 110 including one or more condom packages 130 disposed adjacent to one or more wipe packages 140. Each of the one or more condom packages 130 includes a condom 134 within a container 132. Each condom 134 is rolled in conventional fashion and individually packaged. Each condom 134 may be selected for the prophylactic kit 110 from varying and assorted types such as lubricated and spermicidal. The one or more wipe packages 140 are comprised of at least one cleansing wipe container 142 that itself includes at least one cleansing wipe 144.

The complete package as a kit is preferably a dry, box-like container 120 holding two or more packaged items with the minimal contents comprising a condom 134 in a container 132. The number of items included within a complete package may vary. Preferably, cleansing and prophylactic kit 110 holds three separately packaged cleansing wipes 144 and three separately packaged condoms 134. All six of these items are preferably packaged together to form a single cleansing and prophylactic kit 110. Kit package 120 may be a bag structure, but preferably is box shaped for ease of shipping and display.

Alternative embodiments include additional wipe containers, each wipe container encapsulating wipes containing solution of: (a) over-the-counter lubricant such as Vagisil® Intimate Moisturizer or alternatively Astroglide® Personal Lubricant or ViAmor® Vaginal Moisturizer; (b) nonoxynol-9 and glycerol; (c) sterile water; or (d) a non-irritating, sterile water-based solution.

Figure 2:
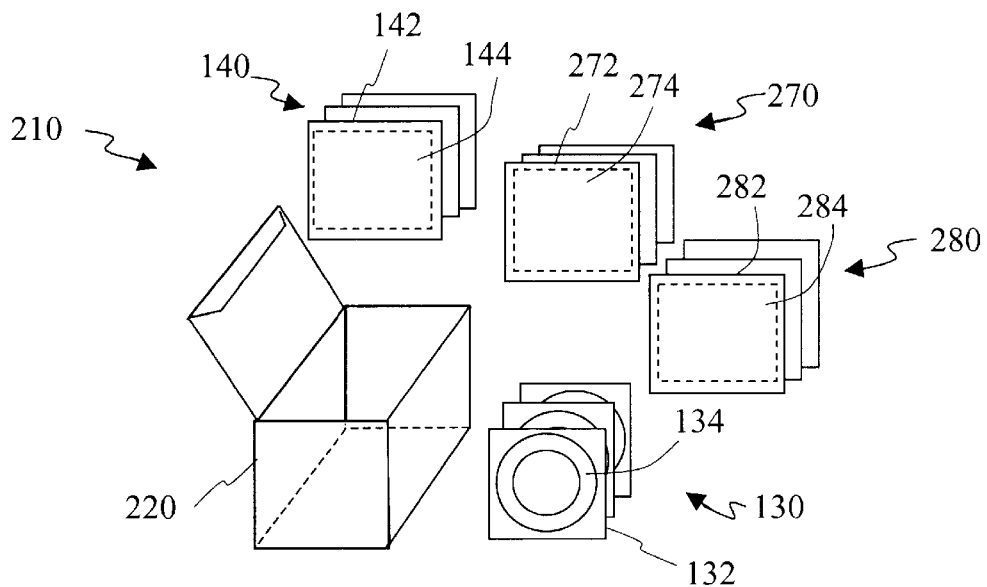
FIG. 2 is an exploded view of the genital cleansing and prophylactic kit illustrating a combination of condoms and wipes of an alternative embodiment.

FIG. 2 is an exploded assembly of an expanded cleansing and prophylactic kit 210 including condom packages 130 disposed adjacent to one or more first wipe packages 140. Each of the one or more condom packages 130 includes a condom 134 within a container 132. Each condom 234 is rolled in conventional fashion and individually packaged. Each condom 134 may be selected for the prophylactic kit 210 from types that may include lubricating or spermicidal coating or both. First wipe packages 140 are comprised of at least one first cleansing wipe container 142 that itself includes at least one first cleansing wipe 144. Second wipe packages 270 are comprised of at least one second cleansing wipe container 272 that itself includes at least one second cleansing wipe 274. Third wipe packages 280 are comprised of at least one third cleansing wipe container 282 that itself includes at least one third cleansing wipe 284. All twelve of these items are preferably packaged together to form a single cleansing and prophylactic kit 210. Kit package 220 may be a bag structure, but preferably is box, as illustrated, shaped for ease of shipping and display.

The first wipe surface-works to deliver the first wipe solution, clean the genital region, and, if a wipe containing nonoxynol-9, or other irritating microbicides, is used before the first wipe, the first wipe is also used to dilute or otherwise reduce the irritating effects of nonoxynol-9, or other irritating microbicides, by reducing or substantially removing the irritating residual solution.

The first wipe surface may be any fabric or material formed by weaving, knitting, pressing, or felting natural or synthetic fibers; or the first wipe surface may be made of a paper material itself made of cellulose pulp, derived mainly from wood, rags, and suitable grasses. Preferably, the first wipe surface is durable enough so that it works to remove fluids from the genital area, including residual solutions of preceding wipes. The first wipe solution may be embedded into, impregnate or saturate the first wipe surface or disposed on top of the first wipe surface.

The first wipe surface of the first cleansing wipe is preferably ten inches or less by eight inches or less with a thickness of sixty mils or less. The first cleansing wipe is foldable so as to fit within the first cleansing wipe container. While the wipe dimensions are ample for the cleansing of the external region of female genitalia, the dimensions and convenience of the wipes satisfy a long-felt need for wipes of substantial size for the cleansing of external regions of the male genitals. In addition, it is preferable that the first cleansing wipe container forms a one inch or less by one inch or less cavity into which a folded first cleansing wipe fits and is hermetically sealed. The third dimension of the cavity is substantially dependent on the thickness of the wipe. The dimensions of first wipe container provide for convenient personal transportation, temporary storage of the used wipe and disposal thereof.

Also as part of the alternative embodiments, the second wipe solution contains nonoxynol-9 and glycerol. Nonoxynol-9 is known to decrease the topical transmission of STDs such as HIV. Glycerol is a syrupy, sweet, colorless or yellowish liquid, $C_3H_8O_3$, obtained from fats and oils as a byproduct of saponification and used as a solvent, an antifreeze, a plasticizer, and a sweetener and in the manufacture of dynamite, cosmetics, liquid soaps, inks, and lubricants. The ratios of nonoxynol-9 to glycerol preferably are one to eight or one to nine by liquid volume. As with the first wipe, the second wipe surface is durable so that it works both to deliver the second wipe solution and clean the genital region. The second wipe surface may be any fabric or material formed by weaving, knitting, pressing, or felting natural or synthetic fibers; or the second wipe surface may be made of a paper material itself made of cellulose pulp, derived mainly from wood, rags, and suitable grasses. The second wipe solution may be embedded into, impregnate or saturate the second wipe surface or disposed on top of the second wipe surface.

The second wipe surface of the second cleansing wipe is preferably ten inches or less by eight inches or less in size and is foldable so as to fit within the second cleansing wipe container. Preferably, the second cleansing wipe container forms a one inch or less by one inch or less cavity into which a folded second cleansing wipe fits and is hermetically sealed. The third dimension is dependent on the thickness of the wipe. Like the first wipe container, the dimensions of second wipe container provide for convenient personal transportation, temporary storage of a used wipe and disposal thereof.

In alternative embodiments, a third cleansing wipe container may be included in the kit with a third cleansing wipe containing of a nonirritating, sterile water-based solution or sterile water. The third cleansing wipe and container are substantially similar to the first and second cleansing wipes in dimensions and consistency so that if used, it would eliminate the need for further cleansing via access to adequate wash facilities such as a shower stall.

Figures 3, 4:
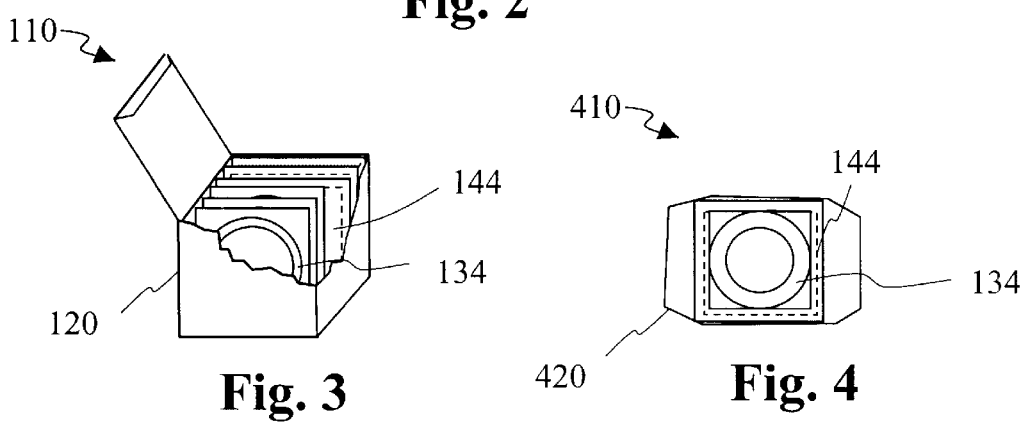
FIG. 3 is a perspective view illustrating the packaged contents of a preferred embodiment.
FIG. 4 illustrates the minimal kit as an alternative embodiment.

FIG. 3 illustrates the packaged contents 110 of a preferred embodiment that includes three separately packaged first cleansing wipes 144 and three separately packaged condoms 134. All six of these items are preferably assembled together in a kit package 120 to form a single cleansing and prophylactic kit 110.

FIG. 4 illustrates the minimal kit 410 to be a plastic bag-like container 420 comprising, as a minimum, a separately packaged condom 134 and a separately packed first cleansing wipe 144.

A method of external genital cleansing and prophylactic kit has been disclosed wherein the kit includes wipes having topical microbicides, personal lubricants, sterile water or sterile water-based solutions disposed on or impregnated therein. Wipes provided in the kit may be used to cleanse the external portions of the genitals before application of the provided condom. After removal of the condom, one or more wipes are to be used to cleanse the external portions of the genitals. The wipes are packaged in conjunction with a condom and when used in accordance with the teaching of the present invention work to inhibit transmission of STDs particularly including HIV.

While certain exemplary embodiments have been described and shown in the accompanying drawings, it is to be understood that such embodiments are merely illustrative of and not restrictive on the broad invention. The scope of each claim term is not limited to the specific constructions and arrangements shown and described, since various other modifications may occur to those ordinarily skilled in the art.

Therefore, the invention has been disclosed by way of example and not limitation, and reference should be made to the following claims to determine the scope of the present invention.

I claim:

1. A prophylactic kit for use in connection with sexual intercourse and related intimate contacts between partners, said prophylactic kit comprises:
   a sealed enclosure, and therein:
      at least one condom;
      at least one first cleansing wipe container; said
      at least one first cleansing wipe container enclosing at least one first cleansing wipe; said
      at least one first cleansing wipe containing a first wipe solution comprised of a personal lubricant, nonirritating to mucosal tissues; and
      at least one second cleansing wipe container;
      said at least one second cleansing wipe container enclosing at least one second cleansing wipe;
      said at least one second cleansing wipe containing a second wipe solution comprised of nonoxynol-9 and glycerol.

2. The prophylactic kit as claimed in claim 1 further comprising at least one third cleansing wipe container; said at least one third cleansing wipe container enclosing at least one third cleansing wipe; said at least one third cleansing wipe containing a third wipe solution comprised of a nonirritating, sterile water-based solution.

3. The prophylactic kit as claimed in claim 1 further comprising at least one third cleansing wipe container; said at least one third cleansing wipe container enclosing at least one third cleansing wipe; said at least one third cleansing wipe containing a third wipe solution comprised of sterile water.

4. A prophylactic kit for use in connection with sexual intercourse and related intimate contacts between partners, said prophylactic kit comprises:
   a sealed enclosure, and therein:
      at least one condom;
      at least one first cleansing wipe container; said
      at least one first cleansing wipe container enclosing at least one first cleansing wipe; said
      at least one first cleansing wipe containing a first wipe solution comprised of a personal lubricant, nonirritating to mucosal tissues; and
      at least one second cleansing wipe container;
      said at least one second cleansing wipe container enclosing at least one second cleansing wipe;
      said at least one second cleansing wipe containing a second wipe solution comprised of nonoxynol-9.

5. The prophylactic kit as claimed in claim 4 further comprising at least one third cleansing wipe container; said at least one third cleansing wipe container enclosing at least one third cleansing wipe; said at least one third cleansing wipe containing a third wipe solution comprised of a nonirritating, sterile water-based solution.

6. The prophylactic kit as claimed in claim 4 further comprising at least one third cleansing wipe container; said at least one third cleansing wipe container enclosing at least one third cleansing wipe; said at least one third cleansing wipe containing a third wipe solution comprised of sterile water.

\* \* \* \* \*